Feb. 5, 1974 R. L. BYRUM Plant Pat. 3,464
PINK ROSE PLANT
Filed May 24, 1972
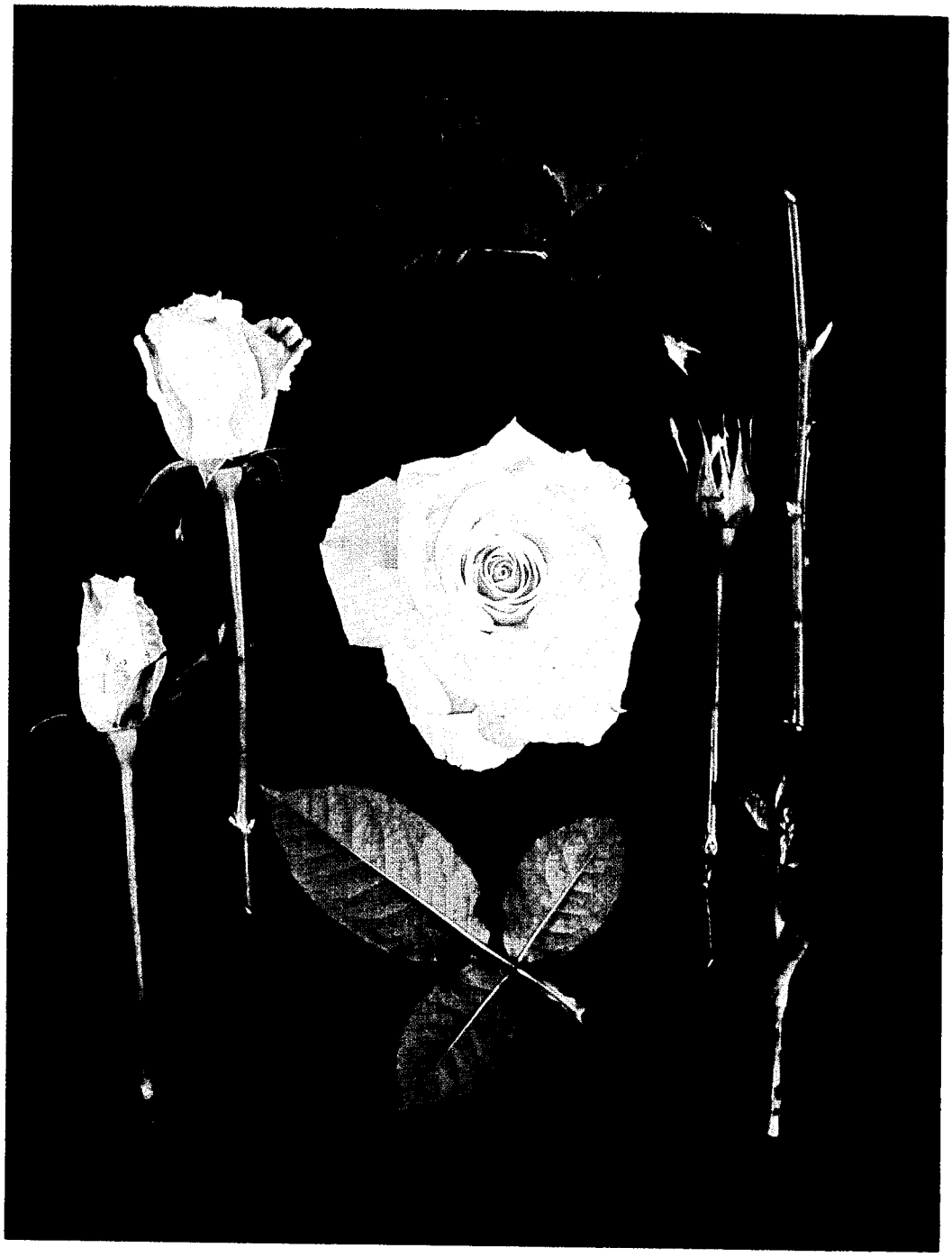

United States Patent Office

Plant Pat. 3,464
Patented Feb. 5, 1974

3,464
ROSE PLANT

Roy L. Byrum, Richmond, Ind., assignor to Joseph H. Hill Company, Richmond, Ind.

Filed May 24, 1972, Ser. No. 256,621
Int. Cl. A01h *5/00*
U.S. Cl. Plt.—18 1 Claim

ABSTRACT OF THE DISCLOSURE

A new variety of greenhouse rose plant distinguished by its free and vigorous growing habit and its excellent production of medium large pink flowers having outer petals with delicate ruffled edges which give the flowers the "Old Lace" effect.

BACKGROUND OF THE INVENTION

This new variety of rose plant was developed in the course of a breeding program carried on by me at Richmond, Ind., with the primary object of improving the character and quality of greenhouse rose plants for the commercial production of cut flowers, and is the result of a crossing of Seventeen (P.P. 1,765) with Jack Frost (P.P. 2,447) made by me in March 1967. This crossing, among others for the same purpose, was done in the hope of finding improved varieties of pink roses and this resulting seedling, upon flowering in October 1968, was found to have a number of distinctive and advantageous characteristics which, if retained, would have considerable value. A particular feature of this new variety, in addition to its vigorus growth habit and abundant production, is its very attractive and unusual flower, very different than the flower of either of its parents, and for that reason it was selected for propagation and test.

Asexual propagation of this new variety of rose plant was done under my direction at Richmond, Ind., by own rooting and at Hamilton City, Calif., by budding, and subsequent asexual propagation at both Hamilton City, Calif., and Richmond, Ind., has proven that the distinctive characteristics of this new variety of rose plant are fixed and hold true from generation to generation.

DESCRIPTION OF THE DRAWING

This new variety of rose plant is illustrated by the accompanying drawing which, in full color as closely true as is reasonably possible by conventional color reproduction processes, shows the form of the newly opened flower, very young wood with new leaves, mature wood, buds in several stages of opening, and the upper and under sides of typical mature leaves.

DESCRIPTION OF THE NEW PLANT

The following is a detailed description of my new variety of rose plant, with color designations according to Koster's Color Guide (K) and Robert S. Wilson's Horticultural Colour Chart (W), based upon observations made at Richmond, Ind., in 1971.

THE PLANT

Origin: Seedling (68–10P)
Parentage:
- Seed parent—Seventeen (P.P. 1,765)
- Pollen parent—Jack Frost (P.P. 2,447)

Classification: Hybrid tea
Form: Bush
Habit: Upright and much branched.
Growth: Free and vigorous
Canes: Medium diameter Main Stems: Color—Scheeles Green 860 (W) overlaid with streaks of Bistres, Plate No. 93 (K)
- *Thorns.*—Several of medium length, hooked downwardly from a short, narrow base. Color—Fawn, Plate No. 89 (K)
- *Prickles and Hairs.*—None Branches: Color—Scheeles Green 860 (W)
- *Thorns.*—Several, of medium length, hooked downwardly from a long, narrow base. Color—Rhodonite Red 0022/3 (W)
- *Prickles and hairs.*—None New shoots: Color—Magenta, Plate No. 50 (K) is nearest
- *Thorns.*—Several, medium length, hooked downwardly from a long, narrow base. Color—Magenta, Plate No. 50 (K)
- *Prickles and hairs.*—None Foliage: Quality—abudant.
- *Leaves.*—Size—medium to large. Shape—odd pinnate. Aspect—moderately heavy. Texture—leathery.
- *Leaflets.*—3 to 5 in number. Shape—ovoid with round base, acuminate apex, and simply serrate margin. Color: Young, upper side—Pod Green 061/2 (W) overlaid with shades of magenta, Plate No. 50 (K) mostly on edges of leaflet, under side—Magenta, Plate No. 50 (K). Mature, upper side—Holly Green, Plate No. 82 (K); under side—Sage Green 000861/1 (W) tinted with shades of Bright Violet, Plate No. 61 (K)
- *Rachis.*—Medium heavy, with grooved upper side and smooth under side
- *Stipules.*—Moderately short length and narrow width, with short points turning outwardly at an angle of less than 45°

*The bud*

Before calyx breaks:
- *Size.*—Medium large
- *Form.*—Long pointed with a conspicuous neck and with foliaceous appendages on the surface of the bud having slender parts extending beyond tip of bud a distance equal to one quarter or more of the bud length
- *Color of calyx.*—Scheeles Green 860/1 (W)

As calyx breaks:
- *Color.*—Outer side of petal—Claret Rose 021/2 (W)

As first petal opens:
- *Size.*—Medium large
- *Forms.*—Long pointed
- *Color.*—Outside—Carmine Rose 621/3 (W). Inside—Porcelain Rose 620/3 (W)

Bud opening: Bud opens up well in greenhouse
Sepals: Permanent, spear shaped, moderately long and curled
- *Colors.*—Inside surfaces—Pod Green 061/3 (W) in central area with a margin of Scheeles Green 860/1 (W). Outside surface—Scheeles Green 860/3 (W)

Peduncle: Medium length, medium diameter and medium strong
- *Bark of penduncle.*—Smooth. Color—Fern Green 0862/1 (W)
- *Thorns.*—None
- *Hairs.*—None
- *Prickles.*—Numerous. Color—Geranium Lake 20/3 (W)

*The flower*

Blooming habit: Abundant and continuous
Size: Medium large—2½ to 3 inches in diameter
Borne: Singly on strong steams of medium length Form: Full and high centered at first, becoming globular-high centered as flower matures. Petals remain tightly rooled outwardly at first, becoming loosely rolled outwardly at maturity Petalage: Very double, with 30 to 35 petals arranged regularly

*Shape of petals.*—Obovate, with mucronate apex and one notch

*Texture.*—Moderately thick

*Appearance.*—Inside—Satiny. Outside—Shiny.

Color:

A newly open flower in greenhouse February 1971:

*Outside petals.*—Outer surfaces: Rose Pink 427/2 (W). Inside surface: Drawn Pink 423/3 (W)

*Intermediate and inner petals.*—Outside surface: Rose Pink 427 (W). Inside surface: Rose Pink 427/3 (W)

A flower opened for three days, October 1971:

*Outside petals.*—Outer surface: White overlaid with Rose Pink 428/3 (W). Inside surface: White overlaid with Rose Pink 427/3 (W) with base of petals showing a very light touch of Primrose Yellow 601/3 (W)

*Intermediate and inner petals.*—Outside surface: White outlaid with Rose Pink 427/3 (W). Inside surface: White overlaid with Rose Pink 427/3 (W) with base of petals showing a very light touch of Primose Yellow 601/3 (W)

General color effect of the open bloom:

*Newly open flower.*—Dawn Pink 523/3 (W)

*Three days opened flower.*—Rose Pink 427/3 (W)

Persistence: Petals hang on

Fragrance: Moderate tea

Lasting quality: 4 to 5 days in October 1971 and at living room temperature

*Reproductive organs*

Stamens: Medium in number

*Filaments.*—Medium in length, most with anthers. Color—Pure White, Plate No. 1 (K)

*Anthers.*—Medium to large in size—all open at once. Color—Saffon Yellow 7/2 (W)

*Pollen.*—Color—Straw Yellow 604/3 (W)

Pistils: Many in number

*Styles.*—Uniform medium length, thin and bunched. Color—Creamy White, Plate No. 2 (K)

*Stigmas.*—Color—Primrose Yellow 601/3 (W)

Ovularies: Some protruding from calyx

Seeds: None

This new variety of rose plant is particularly notable because of the remarkable development of the flower upon its opening from the bud. The outer petals develop delicate ruffled edges as the flower opens and when the flower is fully opened, it resembles the bloom of a Pink Perfection camellia both in size and color. This plant has longer pointed buds than its parents, is a free grower with excellent production, and has few thorns. The plant is a material improvement over either of its parents in that it propagates better and produces larger flowers on longer stems than its seed parent and is of vastly different color than its pollen parent.

I claim:

1. A new and distinct variety of rose plant substantially as herein shown and described, characterized by its vigorous growth and excellent production of relatively large pale pink flowers which open from a long pointed bud to the form of a camellia.

No reference cited.

ROBERT E. BAGWILL, Primary Examiner